(12) United States Patent
Metz

(10) Patent No.: US 8,399,709 B2
(45) Date of Patent: Mar. 19, 2013

(54) METHOD FOR THE SULFONYLATION OF A HYDROXYLATED ORGANIC COMPOUND

(75) Inventor: François Metz, Irigny (FR)

(73) Assignee: Rhodia Operations, Aubervilliers (FR)

( * ) Notice: Subject to any disclaimer, the term of this patent is extended or adjusted under 35 U.S.C. 154(b) by 27 days.

(21) Appl. No.: 12/994,393

(22) PCT Filed: May 28, 2009

(86) PCT No.: PCT/EP2009/056554
§ 371 (c)(1),
(2), (4) Date: Mar. 23, 2011

(87) PCT Pub. No.: WO2009/144281
PCT Pub. Date: Dec. 3, 2009

(65) Prior Publication Data
US 2011/0190542 A1    Aug. 4, 2011

(30) Foreign Application Priority Data
May 29, 2008   (FR) ..................................... 08 02943

(51) Int. Cl.
*C07C 303/28*   (2006.01)
(52) U.S. Cl. .......................................... 568/32; 568/24
(58) Field of Classification Search .................... 568/32, 568/24
See application file for complete search history.

(56) References Cited

U.S. PATENT DOCUMENTS

| 3,346,612 | A | * | 10/1967 | Hansen | ........................... 558/54 |
| 3,419,595 | A | * | 12/1968 | Hansen | ........................... 558/54 |
| 5,550,273 | A | * | 8/1996 | Savu | ............................... 558/54 |
| 2008/0058538 | A1 | * | 3/2008 | Matsunaga et al. | ........... 549/463 |

FOREIGN PATENT DOCUMENTS

| EP | 0646575 A1 | * | 5/1995 |
| WO | WO 0228826 | | 4/2002 |

OTHER PUBLICATIONS

International Search Report: International Application No. PCT/EP2009/056554; dated Jul. 20, 2009.

* cited by examiner

*Primary Examiner* — Sudhakar Katakam
*Assistant Examiner* — Pancham Bakshi
(74) *Attorney, Agent, or Firm* — Hunton & Williams, LLP

(57) ABSTRACT

The subject of the present invention is a method for the sulphonylation of a hydroxylated organic compound. The invention relates more particularly to a method for the trifluoromethanesulphonylation of a hydroxylated organic compound. The invention is especially intended for perfluorinated aliphatic hydroxylated compounds. The method of the invention for the sulphonylation of a hydroxylated organic compound is characterized in that it comprises reacting said compound with a sulphonylation agent in an organic medium and in the presence of a heterogeneous inorganic base.

27 Claims, No Drawings

METHOD FOR THE SULFONYLATION OF A HYDROXYLATED ORGANIC COMPOUND

CROSS-REFERENCE TO RELATED APPLICATIONS

This application is the U.S. National Phase of International Application No. PCT/EP2009/056554 filed on May 28, 2009, which claims priority to French Application No. FR 08/02943 filed May 29, 2008, both of which are incorporated by reference herein in their entireties.

FIELD OF THE INVENTION

The subject matter of the present invention is a process for the sulfonylation of a hydroxylated organic compound.

The invention relates more particularly to a process for the trifluoromethanesulfonylation of a hydroxylated organic compound.

The invention is targeted in particular at hydroxylated compounds of aliphatic type and more particularly those which comprise a perfluorinated aliphatic chain.

The invention preferably applies to perfluorinated aliphatic alcohols and in particular to 2,2,2-trifluoroethanol.

BACKGROUND

It is known, according to FR-A 1 470 669, to prepare trifluoroethyl triflate ($CF_3SO_3CH_2CF_3$), referred to simply as "TfOTFE", by reaction of 2,2,2-trifluoroethanol with triflyl chloride ($CF_3SO_2Cl$) in the presence of a base, such as triethylamine, and in an organic solvent which is dichloromethane.

The disadvantage from which this process suffers is that it results in highly polluting discharges due to the presence of large amounts of ammonium salt.

Provision has been made, according to EP-A 1 322 601, for a process for the sulfonylation of a hydroxylated organic compound which consists of reacting said compound with a sulfonylating agent in the presence of an effective amount of a Lewis acid.

The Lewis acid is a compound comprising a metal or semimetal cation regarded as "intermediate" in the "hardness" and "softness" classification defined by R. Pearson. Antimony chloride is an example of a Lewis acid suitable for the process described in EP-A 1 322 601.

Although this catalysis is highly advantageous, the Applicant Company was looking for a process involving commoner reactants.

DETAILED DESCRIPTION OF PREFERRED EMBODIMENTS

The object of the present invention is to provide a process which makes it possible to avoid the abovementioned disadvantages.

There has now been found, and it is this which forms the subject matter of the present invention, a process for the sulfonylation of a hydroxylated organic compound, characterized in that it comprises the reaction of said compound with a sulfonylating agent in an organic medium and in the presence of a heterogeneous inorganic base.

In its preferred alternative form, the invention is targeted at a process for the trifluoromethanesulfonylation of a hydroxylated organic compound, characterized in that it comprises the reaction of said compound with a trifluoromethanesulfonylating agent in an organic medium and in the presence of a heterogeneous inorganic base.

The hydroxylated organic compound which is involved in the process of the invention corresponds more particularly to the formula (I):

$$R_1—O—H \qquad (I)$$

in said formula (I):
 $R_1$ representing a substituted or unsubstituted hydrocarbon group comprising from 1 to 40 carbon atoms which can be a saturated or unsaturated and linear or branched acyclic aliphatic group, a saturated, unsaturated or aromatic and monocyclic or polycyclic carbocyclic or heterocyclic group, or a sequence of the abovementioned groups.

More specifically, $R_1$ represents a hydrocarbon group having from 1 to 20 carbon atoms which can be a saturated or unsaturated and linear or branched acyclic aliphatic group, a saturated, unsaturated or aromatic and monocyclic or polycyclic carbocyclic or heterocyclic group or a saturated or unsaturated and linear or branched aliphatic group carrying a cyclic substituent.

$R_1$ preferably represents a saturated and linear or branched acyclic aliphatic group preferably having from 1 to 12 carbon atoms and more preferably still from 1 to 4 carbon atoms.

The invention does not exclude the presence of an unsaturation in the hydrocarbon chain, such as one or more double bonds, which may or may not be conjugated, or a triple bond.

The hydrocarbon chain can optionally be interrupted by a heteroatom (for example, oxygen or sulfur) or by a functional group, in so far as the latter does not react, and mention may in particular be made of a group such as in particular —CO—.

The hydrocarbon chain can optionally carry one or more substituents (for example, halogen, ester or aldehyde), in so far as it does not interfere with the sulfonylation reaction.

Thus, the hydrocarbon chain preferably carries one or more fluorine atoms.

The saturated or unsaturated and linear or branched acyclic aliphatic group can optionally carry a cyclic substituent. The term "ring" is understood to mean a saturated, unsaturated or aromatic carbocyclic or heterocyclic ring.

The acyclic aliphatic group can be connected to the ring via a valency bond, a heteroatom or a functional group, such as oxy, carbonyl, carboxyl, sulfonyl, and the like.

It is possible to envisage, as examples of cyclic substituents, cycloaliphatic, aromatic or heterocyclic substituents, in particular cycloaliphatic substituents comprising 6 carbon atoms in the ring or benzene substituents, these cyclic substituents themselves optionally carrying any substituent, in so far as they do not interfere with the reactions involved in the process of the invention. Mention may in particular be made of alkyl or alkoxy groups having from 1 to 4 carbon atoms.

Targeted more particularly among the aliphatic groups carrying a cyclic substituent are the aralkyl groups having from 7 to 12 carbon atoms, in particular benzyl or phenylethyl.

In the formula (I), $R_1$ can also represent a saturated or unsaturated carbocyclic group preferably having 5 or 6 carbon atoms in the ring, a saturated or unsaturated heterocyclic group comprising in particular 5 or 6 atoms in the ring, including 1 or 2 heteroatoms, such as nitrogen, sulfur and oxygen atoms, a monocyclic aromatic carbocyclic or heterocyclic group, preferably phenyl or pyridyl, or a fused or nonfused polycyclic aromatic carbocyclic or heterocyclic group, preferably naphthyl.

Since $R_1$ comprises a ring, the latter can also be substituted. The number of substituents is generally at most 4 per ring but is most often equal to 1 or 2. The nature of the substituent is not important in so far as it does not react under the conditions of the invention, in particular with a strong base. Mention may be made, as examples of substituent, in particular of alkyl or alkoxy groups having from 1 to 4 carbon atoms or halogen atoms.

The invention does not exclude the case where the hydroxylated organic compound is difunctional, that is to say that it carries another OH group carried by an aliphatic chain or as substituent of an aromatic ring.

Mention may be made, as more specific examples, of the following linkage of aromatic rings optionally carrying substituents:

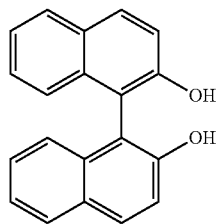 [SMILES: Oc1ccc2ccccc2c1-c1c(O)ccc2ccccc12]

Among all the meanings given above for $R_1$, $R_1$ is preferably a linear or branched alkyl group having from 1 to 12 carbon atoms and preferably from 1 to 4 carbon atoms.

The process of the invention applies very particularly to aliphatic alcohols and more particularly to fluorinated and perfluorinated alcohols corresponding to the formula (Ia):

$$R_1\text{—}O\text{—}H \quad \text{(Ia)}$$

in said formula (Ia) $R_1$ representing a fluorinated or perfluorinated alkyl chain comprising from 1 to 10 carbon atoms and from 1 to 21 fluorine atoms, preferably from 3 to 21 fluorine atoms.

The invention relates more particularly to the perfluorinated aliphatic alcohols corresponding to the formula (Ia) in which $R_1$ represents a perfluorinated alkyl chain comprising from 1 to 10 carbon atoms and from 3 to 21 fluorine atoms.

The process of the invention applies particularly well to the compounds of formula (I) or (Ia) such as ethanol, 2,2,2-trifluoroethanol, 2,2-difluoroethanol, 1,1-difluoroethanol, pentafluoroethanol, hexafluoroisopropanol, pentafluorophenol, p-nitrophenol or p-(trifluoromethyl)phenol.

As regards the sulfonylating agent, is a halide of a perfluoroalkylsulfonic acid.

It corresponds more particularly to the following formula (II):

in said formula (II):
$R_2$ representing a perfluoroalkyl hydrocarbon group of $R_f$ type having from 1 to 10 carbon atoms,
Z represents a fluorine, chlorine or bromine atom.
In the formula (II), the choice is preferably made of the case where Z is a chlorine or bromine atom. Z is more particularly a bromine atom.

$R_f$ defines a group corresponding to the following formula $C_pH_aF_b$, in which p represents a number ranging from 1 to 10, b represents a number ranging from 3 to 21 and a+b=2p+1.

More preferably, p is a number ranging from 1 to 8 and b is a number ranging from 3 to 17.

The preferred sulfonylating agents correspond to the formula (II) in which the —$SO_2$—$R_2$ group represents:
a trifluoromethanesulfonyl (triflyl) group —$SO_2$—$CF_3$,
a pentafluoroethanesulfonyl group —$SO_2$—$C_2F_5$,
a nonafluorobutanesulfonyl (nonaflyl) group —$SO_2$—$C_4F_9$,
a perfluorooctanesulfonyl group —$SO_2$—$C_8F_{17}$.

The $R_f$ group is more preferably a $CF_3$ group or a $CF_2$—$CF_3$ group.

The preferred sulfonylating agent according to the invention, which is known as "trifluoromethanesulfonylating agent", corresponds to the formula (II) in which $R_2$ represents a $CF_3$ group and Z represents a fluorine, chlorine or bromine atom.

Recourse is thus preferably had, as preferred examples of sulfonylating agents, to trifluoromethanesulfonyl fluoride, to trifluoromethanesulfonyl chloride or to trifluoromethanesulfonyl bromide.

Trifluoromethanesulfonyl bromide is preferred.

According to the process of the invention, the reaction between the hydroxylated organic compound and the sulfonylating agent is carried out in the liquid phase in the presence of an organic solvent and of a base.

The ratio of the number of moles of sulfonylating agent to the number of moles of hydroxylated organic compound can vary between 0.5 and 2 and is preferably between 0.8 and 1.2.

A base is involved in the process of the invention, the role of which is to trap the hydrohalic acid formed by the reaction.

Recourse may be had to a hydroxide of ammonium or of a monovalent metal and/or of a divalent metal, preferably a hydroxide of an alkali metal and/or of an alkaline earth metal.

Mention may be made, as more specific examples of bases to be used, of an alkali metal hydroxide, such as a hydroxide of sodium, potassium or cesium, an alkaline earth metal hydroxide, such as a hydroxide of magnesium, calcium or barium, or a hydroxide of a metal from Group IIb, such as zinc.

In the present text, reference is made hereinbelow to the Periodic Table of the Elements published in the Bulletin de la Société Chimique de France, No. 1 (1966).

The choice is preferably made, among the bases, of sodium hydroxide or potassium hydroxide.

Another category of bases which can be used in the process of the invention is composed of alkali metal or alkaline earth metal carbonates or hydrogencarbonates.

The choice is more preferably made of sodium carbonate or potassium carbonate.

According to one characteristic of the process of the invention, the base is employed in a solid form, generally in the form of a powder and more particularly in a ground form in the case of the alkali metal or alkaline earth metal hydroxides, in particular in the case of sodium hydroxide, potassium hydroxide and lithium hydroxide.

The operation of grinding the base can be carried out in any type of mill resistant to corrosion by the base (for example made of stainless steel).

The amount of base employed is such that the ratio of the number of moles of base to the number of moles of sulfonylating agent preferably varies between 1 and 2 and more preferably between 1.4 and 1.6.

The reaction is carried out in the presence of an organic solvent.

A solvent which is inert under the reaction conditions is chosen.

The appropriate solvents are nonpolar organic solvents, such as halogenated or nonhalogenated aliphatic, cycloaliphatic or aromatic hydrocarbons, or more polar organic solvents, such as, in particular, ethers or nitriles.

Mention may be made, as nonlimiting examples of such solvents, of aliphatic and cycloaliphatic hydrocarbons, more particularly paraffins, such as, in particular, hexane, heptane, octane, isooctane, nonane, decane, undecane, tetradecane, petroleum ether and cyclohexane, or aromatic hydrocarbons, such as, in particular, benzene, toluene, xylenes, ethylbenzene, diethylbenzenes, trimethylbenzenes, cumene, pseudocumene or petroleum fractions composed of mixtures of alkylbenzenes, in particular the fractions of Solvesso® type.

Recourse may also be had to aliphatic or aromatic halogenated hydrocarbons and mention may be made of perchlorinated hydrocarbons, such as, in particular, trichloromethane or tetrachloroethylene, partially chlorinated hydrocarbons, such as dichloromethane, dichloroethane, tetrachloroethane, trichloroethylene, 1-chlorobutane or 1,2-dichlorobutane, monochlorobenzene, dichlorobenzenes or their mixtures, trifluoromethylbenzene or trifluoromethoxybenzene.

Ethers can also be used as solvents. Mention will be made, for example, of aliphatic, cycloaliphatic or aromatic ethers and more particularly methyl tert-butyl ether, dipentyl ether, diisopentyl ether, ethylene glycol dimethyl ether (or 1,2-dimethoxyethane) or diethylene glycol dimethyl ether (or 1,5-dimethoxy-3-oxapentane), or cyclic ethers, for example dioxane or tetrahydrofuran.

It is also possible to choose a solvent of nitrile type. Mention may in particular be made of aliphatic or aromatic nitriles, preferably acetonitrile, propionitrile, butanenitrile, isobutanenitrile, pentanenitrile, 2-methylglutaronitrile, adiponitrile, benzonitrile, tolunitriles, malonitrile or 1,4-benzonitrile.

In accordance with the process of the invention, it has been found, surprisingly, that the yield of the sulfonylation reaction carried out in the presence of a heterogeneous inorganic base was particularly high provided that recourse was had to a nonpolar organic solvent.

Nonpolar organic solvents are preferably employed in the process of the invention.

Thus, the preferred solvents for the implementation of the process of the invention are xylenes, chlorobenzene and dichlorobenzenes or their mixtures.

Use will also be made of a mixture of organic solvents.

The amount of organic solvent employed is preferably chosen such that the concentration by weight of a sulfonylating agent in the solvent is between 5 and 50%, preferably between 20 and 40%.

According to a preferred alternative form of the process of the invention, the choice is made to operate under anhydrous conditions. However, is possible to tolerate a small amount of water in the reaction medium, preferably of less than 1% by weight and more preferably of less than 0.5% by weight.

The reaction is generally carried out at a temperature of between 0° C. and the reflux temperature of the organic solvent, preferably at a temperature of between 15° C. and 30° C.

The sulfonylation reaction is generally carried out at atmospheric pressure but preferably under a controlled atmosphere of inert gases. An atmosphere of rare gases, preferably argon, can be established but it is more economic to use nitrogen. A pressure slightly greater or lower than atmospheric pressure may be suitable.

The process of the invention is simple to carry out.

The reactants can be introduced according to numerous alternative forms but some are preferred.

A first embodiment consists in preparing a heel composed of the hydroxylated organic compound and the inorganic base and in then gradually introducing, preferably by running in, the sulfonylating agent introduced in the organic solvent.

Another embodiment, which exhibits the advantage of facilitating the stirring of the reaction medium, is to form a heel comprising the inorganic base and the organic solvent and to then gradually introduce, preferably by running in together, the sulfonylating agent and the hydroxylated organic compound.

After keeping the reaction medium stirred at the chosen temperature, there is obtained, at the end of the reaction, a sulfonic ester corresponding to the following formula:

$$R_1OSO_2R_2 \qquad (III)$$

in said formula $R_1$ and $R_2$ having the meanings given above.

The product obtained is recovered conventionally. Generally, water is added, which makes it possible to recover, in the aqueous phase, the salts formed.

The aqueous and organic phases are separated.

The organic phase is collected and optionally washed.

The sulfonic ester is recovered from the organic phase according to the techniques conventionally used.

It is possible, for example, to carry out a distillation or an extraction using an organic solvent chosen so that it does not form an azeotrope with water.

The process of the invention thus makes it possible to obtain the ester in a simple way with a good yield and a good selectivity.

Another advantage of the process of the invention is that it makes it possible to employ a sulfonylating agent of bromide type which exhibits the characteristic of being much less volatile than a sulfonylating agent of chloride type, which is particularly advantageous from an industrial viewpoint.

The examples which follow illustrate the invention without, however, limiting it.

Examples 1 to 5 correspond to the sulfonylation of trifluoroethanol in the presence of a heterogeneous base (solid potassium carbonate), with the exception of example 4, which involves an aqueous potassium carbonate solution.

Example 6 relates to the sulfonylation of ethanol in the presence of a heterogeneous base.

Examples 7 to 10 are comparative tests in which the base is a nitrogenous organic base.

Example 11 relates to the sulfonylation of ethanol using trifluoromethanesulfonyl chloride in the presence of a heterogeneous base.

In the examples, the following abbreviations signify:

TFE: TriFluoroEthanol,

TFSBr: TriFluoromethaneSulfonyl Bromide (triflyl bromide),

TFSCl: TriFluoromethaneSulfonyl Chloride (triflyl chloride),

ACN: ACetoNitrile,

MCB: MonoChloroBenzene,

ODCB: OrthoDiChloroBenzene.

The degree of conversion (DC) of the triflyl bromide or chloride ($CF_3SO_2Br$ or $CF_3SO_2Cl$) corresponds to the ratio of the number of moles of triflyl bromide or chloride converted to the number of moles of triflyl bromide or chloride introduced.

The TfOTFE yield ($RY_{TfOTFE}$) corresponds to the ratio of the number of moles of TfOTFE formed to the number of moles of triflyl, bromide or chloride introduced.

The TfOEt yield ($RY_{TfOEt}$) corresponds to the ratio of the number of moles of TfOEt (ethyl triflate) formed to the number of moles of triflyl bromide or chloride introduced.

The TfOTFE selectivity ($S_{TfOTFE}$) corresponds to the ratio the number of moles of TfOTFE formed to the number of moles of triflyl bromide or chloride converted.

Examples 1 to 5

The following are introduced under nitrogen into a 150 ml glass reactor:

| | |
|---|---|
| $K_2CO_3$ | 7 g (50.14 mmol) |
| TFE | 3.2 g (32 mmol) |
| solvent | 7 g |

The resulting heterogeneous medium is brought with stirring to a temperature T mentioned in the following table (I) and then TFSBr (7 g, 32 mmol), diluted with TFE (3.2 g, 32 mmol) or with a solvent (7 g), is added over a time t also mentioned in table (I).

After the addition, the reaction medium is maintained at the temperature T' for a time t' mentioned in table (I) and then the reactants and the products obtained are quantitatively determined by $^{19}F$ NMR.

The results obtained are recorded in table (I).

TABLE (I)

| | | REACTION | | | MAINTENANCE | | | | |
|---|---|---|---|---|---|---|---|---|---|
| Ex. | Reactants in heel | T in heel (° C.) | Reactants run in | Running-in time (h) | T' (° C.) | t' (h) | DC (%) | RY (%) | S (%) |
| 1 | $K_2CO_3$/ TFE/ACN | 55° C.-60° C. | TFSBr/ ACN | 1 | 60° C. | 1 | 94 | 62 | 66 |
| 2 | $K_2CO_3$/ TFE/MCB | 40° C. | TFSBr/ MCB | 1.5 | 40° C. | 0.5 | 85 | 82 | 96 |
| 3 | $K_2CO_3$/ ODCB | 25° C. | TFSBr/ TFE ((1/2) | 1 | 25° C. | 0.5 | 45 | 89* | 89 |
| 4 | $K_2CO_3$/ TFE/$H_2O$ | 40° C. | TFSBr/ ODCB | 1.5 | 40° C. | 0.7 | 44 | 27 | 61 |
| 5 | $K_2CO_3$/ xylenes | 25° C. | TFSBR/ TFE (1/2) | 1.2 | 25° C. | 0.8 | 56 | 95* | 95 |

*= calculated with respect to the TFSBr.

Example 6

The following are introduced under nitrogen into a 150 ml glass reactor:

| | |
|---|---|
| $K_2CO_3$ | 7 g (50.14 mmol) |
| EtOH | 3.2 g (32 mmol) |
| ODCB | 25 g |

The resulting heterogeneous medium is brought with stirring to 25° C. and then the TFSBr (7 g, 32 mmol), diluted with EtOH (1.5 g, 31 mmol), is added over 1 h.

After the addition, the reaction medium is maintained at 25° C. for 1 h.

The results obtained are as follows:

DC=100%, $RY_{TfOEt}$=53% (calculated with respect to the TFSBr).

Comparative Examples 7 to 10

The following are introduced under nitrogen into a 150 ml glass reactor:

| | |
|---|---|
| TFE | 7.05 g (70.5 mmol) |
| tertiary amine $NR_3$ | 7.2 g (70.5 mmol) |
| solvent | 14 g |

The resulting solution is brought with stirring to the temperature T mentioned in the following table (II) and then the TFSBr (15 g, 70.5 mmol), diluted or not with a solvent (14 g), is added over a time t also mentioned in table (II).

After the addition, the reaction medium is maintained at the temperature T' for a time t' mentioned in table (II) and then the reactants and the products obtained are quantitatively determined by $^{19}F$ NMR.

The corresponding results are collated in the following table (II):

TABLE (II)

| | | REACTION | | | MAINTENANCE | | | | |
|---|---|---|---|---|---|---|---|---|---|
| Ex. | Reactants in heel | T in heel (° C.) | Reactants run in | Running-in time (h) | T' (° C.) | t' (h) | DC (%) | RY (%) | S (%) |
| 7 | TFE/$NEt_3$ | 0 | TFSBr | 2 | 0 | 1 | 100 | 12 | 12 |
| 8 | TFE/$NEt_3$ | 60 | TFSBr | 1.7 | 60 | 0.3 | 100 | 0 | 0 |
| 9 | TFE/$NEt_3$/ ACN | 60 | TFSBr/ACN | 1.5 | 60 | 0.3 | 100 | 0 | 0 |

TABLE (II)-continued

| | REACTION | | | | | | | |
|---|---|---|---|---|---|---|---|---|
| | Reactants | T in heel | Reactants | Running-in time | MAINTENANCE | | DC | RY | S |
| Ex. | in heel | (° C.) | run in | (h) | T' (° C.) | t' (h) | (%) | (%) | (%) |
| 10 | TFE/ NEt$_2$i-Pr | 0 | TFSBr | 3 | 0 | 1 | 100 | 0 | 0 |

Example 11

Example 6 is repeated, with the only difference that TFSCl (5.35 g, 32 mmol) is employed, to give the following results:
DC=100%,
RY$_{TfOEt}$=51% (calculated with respect to the TFSCl).

What is claimed is:

1. A process for the sulfonylation of a hydroxylated organic compound, comprising reacting said hydroxylated organic compound with a sulfonylating agent in an organic medium in the presence of a solid inorganic base,
wherein the reaction is carried out under anhydrous conditions.

2. The process of claim 1, wherein the hydroxylated organic compound comprises a compound of formula (I):

$$R_1\text{—}O\text{—}H \quad (I)$$

wherein:
R$_1$ represents a substituted or unsubstituted hydrocarbon group comprising from 1 to 40 carbon atoms.

3. The process of claim 2, wherein R$_1$ represents a saturated or unsaturated, linear or branched acrylic aliphatic group; a saturated, unsaturated, or aromatic, monocyclic or polycyclic, carbocyclic or heterocyclic group; or a combination thereof.

4. The process of claim 2, wherein the hydroxylated organic compound comprises an aliphatic alcohol of formula (I), wherein R$_1$ represents a saturated, linear or branched, acyclic aliphatic group having from 1 to 12 carbon atoms.

5. The process of claim 2, wherein the hydroxylated organic compound comprises a fluorinated or perfluorinated aliphatic alcohol of formula (Ia):

$$R_1\text{—}O\text{—}H \quad (Ia)$$

wherein R$_1$ represents a fluorinated or perfluorinated alkyl chain comprising from 1 to 10 carbon atoms and from 1 to 21 fluorine atoms.

6. The process claim 2, wherein the hydroxylated organic compound comprises ethanol, 2,2,2-trifluoroethanol, 2,2-difluorethanol, 1,1-difluoroethanol, pentafluoroethanol, hexafluoroisopropanol, pentafluorophenol, p-nitrophenol, p-(trifluoromethyl)phenol, or a mixture thereof.

7. The process of claim 1, wherein the sulfonylating agent comprises a halide of a perfluoroalkylsulfonic acid of formula (II):

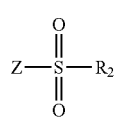

(II)

wherein:
R$_2$ represents a perfluoroalkyl hydrocarbon group having from 1 to 10 carbon atoms, and
Z represents a fluorine, chlorine, or bromine atom.

8. The process of claim 7, wherein the perfluoroalkyl hydrocarbon group comprises a group of formula C$_p$H$_a$F$_b$, wherein p represents a number ranging from 1 to 10, b represents a number ranging from 3 to 21, and a=(2p+1)–b.

9. The process of claim 7, wherein R$_2$ represents a CF$_3$ group or a CF$_2$—CF$_3$ group.

10. The process of claim 7, wherein Z comprises a chlorine or bromine atom.

11. The process of claim 9, wherein R$_2$ represents a CF$_3$ group and Z represents a fluorine, chlorine, or bromine atom.

12. The process of claim 1, wherein the sulfonylating agent comprises trifluoromethanesulfonyl fluoride, trifluoromethanesulfonyl chloride, or trifluoromethanesulfonyl bromide.

13. The process of claim 1, wherein the ratio of the number of moles of sulfonylating agent to the number of moles of hydroxylated organic compound ranges from 0.5 to 2.

14. The process of claim 1, wherein the base comprises a hydroxide of a monovalent metal and/or divalent metal; an alkali metal or alkaline earth metal carbonate or hydrogencarbonate; or a combination thereof.

15. The process of claim 14, wherein the base comprises sodium carbonate or potassium carbonate.

16. The process of claim 1, wherein the base comprises a solid, a powder, or, if the base is a hydroxide, a ground hydroxide.

17. The process of claim 1, wherein the ratio of the number of moles of base to the number of moles of sulfonylating agent ranges from 1 to 2.

18. The process of claim 1, wherein the reaction is carried out in the presence of an organic solvent.

19. The process of claim 18, wherein the organic solvent comprises a halogenated or non-halogenated aliphatic, cycloaliphatic, or aromatic hydrocarbon; an ether; a nitrile; or a combination thereof.

20. The process of claim 18, wherein the organic solvent comprises a non-polar organic solvent.

21. The process of claim 20, wherein the non-polar organic solvent comprises a halogenated or nonhalogenated aliphatic, cycloaliphatic, or aromatic hydrocarbon.

22. The process of claim 18, wherein the reaction is carried out at a temperature ranging from 0° C. to the reflux temperature of the organic solvent.

23. The process of claim 22, wherein the temperature ranges from 15° C. to 30° C.

24. The process of claim 18, wherein said process comprises preparing a heel comprising the hydroxylated organic compound and the inorganic base and then gradually introducing the sulfonylating agent into the organic solvent.

25. The process of claim 18, wherein said process comprises forming a heel comprising the inorganic base and the organic solvent and in then gradually introducing the sulfonylating agent and the hydroxylated organic compound.

26. The process of claim 1, comprising reacting 2,2,2-trifluoroethanol and trifluoromethanesulfonyl bromide.

27. A process for the sulfonylation of a hydroxylated organic compound, comprising reacting said hydroxylated organic compound with a sulfonylating agent in an organic solvent in the presence of a solid inorganic base, wherein:

the reaction is carried out under anhydrous conditions,
said base traps hydrohalic acid formed by the reaction, and
the reaction does not form an ammonium salt.

* * * * *

UNITED STATES PATENT AND TRADEMARK OFFICE
CERTIFICATE OF CORRECTION

PATENT NO.       : 8,399,709 B2                                         Page 1 of 1
APPLICATION NO.  : 12/994393
DATED            : March 19, 2013
INVENTOR(S)      : François Metz It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 142 days.

Signed and Sealed this
First Day of September, 2015

Michelle K. Lee
*Director of the United States Patent and Trademark Office*